United States Patent [19]

Hirowatari et al.

[11] Patent Number: 5,565,609
[45] Date of Patent: Oct. 15, 1996

[54] METHOD OF PURIFYING AROMATIC DICARBOXYLIC ACIDS

[75] Inventors: Noriyuki Hirowatari; Hiroyasu Ohno; Kenji Shimamoto, all of Yamaguchi, Japan

[73] Assignee: Mitsui Petrochemical Industries, Ltd., Tokyo, Japan

[21] Appl. No.: 313,184

[22] PCT Filed: Feb. 9, 1994

[86] PCT No.: PCT/JP94/00197

§ 371 Date: Nov. 22, 1994

§ 102(e) Date: Nov. 22, 1994

[87] PCT Pub. No.: WO94/18152

PCT Pub. Date: Aug. 18, 1994

[30] Foreign Application Priority Data

Feb. 12, 1993 [JP] Japan .................................. 5-047371
Feb. 12, 1993 [JP] Japan .................................. 5-047372
Jul. 2, 1993 [JP] Japan .................................. 5-190869

[51] Int. Cl.$^6$ ............................................. C07C 51/42
[52] U.S. Cl. .......................... 562/485; 562/486; 562/487
[58] Field of Search ................................... 562/485, 486, 562/487

[56] References Cited

U.S. PATENT DOCUMENTS 2,664,440 12/1953 Toland, Jr. .
3,059,025 10/1962 Knobloch et al. .
4,605,762 8/1986 Mandoki ...................................... 562/83
5,045,122 9/1991 Tindall et al. ............................. 134/29
5,344,969 9/1994 Iwane et al. ............................ 562/486

FOREIGN PATENT DOCUMENTS 47-38941 12/1972 Japan .
48-10037 2/1973 Japan .
49-102636 9/1974 Japan .
50-135062 10/1975 Japan .
50-142542 11/1975 Japan .

OTHER PUBLICATIONS

Derwent Information Ltd, 78–12944A, 1975.

Chemical Abstracts, 84:121553, Yamamoto et al, 1975.

Primary Examiner—Samuel Barts
Attorney, Agent, or Firm—Birch, Stewart, Kolasch & Birch, LLP

[57] ABSTRACT

There is provided a method of purifying a crude aromatic dicarboxylic acid which comprises purifying an aqueous solution of an organic amine salt of the crude aromatic dicarboxylic acid, and then thermally decomposing the organic amine salt whereby to recover the thus highly purified aromatic dicarboxylic acid.

14 Claims, No Drawings

METHOD OF PURIFYING AROMATIC DICARBOXYLIC ACIDS

This application was filed under U.S.C. 371 from the application PCT/JP94/00197 filed Feb. 9, 1994.

BACKGROUND OF THE INVENTION

1. Technical Field of the Invention

This invention relates to a method of purifying aromatic dicarboxylic acids, more particularly, to a method of purifying and recovering the thus highly purified aromatic dicarboxylic acids via their organic amine salts.

2. Description of the Related Art

From the standpoint of reuse of resources and protection of environment, a variety of resin products are in fact practically recovered and reused, or intensive investigations are conducted for recovery and reuse of resin products.

Certain kinds of polyester resins contains aromatic dicarboxylic acids as structural units. For example, an aromatic dicarboxylic acid such as terephthalic acid is contained in polyethylene terephthalate resins or polybutylene terephthalate resins, whereas naphthalene dicarboxylic acid is contained in polyethylene naphthalene-dicarboxylate resins. Such aromatic dicarboxylic acids are practically recovered together with alkylene glycols by hydrolysis of such polyester resins. However, since molded articles of polyester resins usually contain colorants, when such articles are hydrolyzed, the recovered aromatic dicarboxylic acids are usually colored. Hence, it is necessary that the recovered aromatic dicarboxylic acids be purified so that they can be reused as materials for production of polyester resins.

Terephthalic acid, one of the most widely used aromatic dicarboxylic acids as a material for production of polyester resins, has a low vapor pressure even at a high temperature, so that it is ritually impossible to purify the acid by distillation. Moreover, since the acid is substantially insoluble in many organic solvents, it is also impossible to purify the acid by recrystallization.

However, in general, an aromatic dicarboxylic acid, inclusive of terephthalic acid, forms water soluble salts. Thus, the aromatic dicarboxylic acid can be purified with use of usual purifying means. For example, an aqueous solution containing such a water soluble salt of the acid is prepared and then the solution is decolorized by the use of an adsorbent, such as activated carbon, or the salt is recrystallized from the solution, thereby to purifying the aromatic dicarboxylic acid.

As disclosed in Japanese Patent Publication No. 44-20616, there is already known a method to purify crude terephthalic acid wherein the crude terephthalic acid is reacted with ammonia to form an aqueous solution of diammonium terephthalate, and the solution is decolorized, and is then heated to a temperature of 90°–95° C. so that the salt decomposes and crystallizes as monoammonium terephthalate. The salt is collected by filtration and decomposed at a temperature as high as 200°–210° C. and thus the liberated terephthalic acid having a high purity is recovered. However, the method needs such a high temperature as above-mentioned to decompose the monoammonium terephthalate, and hence the method is not readily put to practical industrial operation.

A further method is also known, as disclosed in Japanese Patent application Laid-open No. 46-1369, wherein an aqueous solution of diammonium salt of crude terephthalic acid or isophthalic acid is reduced, and the solution is heated to convert the diammonium salt to a monoammonium salt. The salt is recovered as a highly purified precipitate, and the precipitate is then heated to liberate terephthalic acid or isophthalic acid having a high purity, followed by recovery of the acid. The method also needs a high temperature, as high as more than 200° C., to decompose the monoammonium salt to liberate terephthalic acid or isophthalic acid. Thus, the method is also not readily put to practical industrial operation.

As set forth above, the known method comprises preparing an aqueous solution of ammonium salt of a crude aromatic dicarboxylic acid, purifying the solution, thermally decomposing the ammonium salt to liberate the aromatic dicarboxylic acid having high purity, and then recovering the acid, and thus has a large number of problems, as above mentioned. In addition, since the ammonium salt of an aromatic dicarboxylic acid does not have a high solubility in water, and a concentrated solution can not be prepared, the method is not efficient as a further problem, an acid amide maybe by-produced when the ammonium salt is decomposed and the acid amide contaminates the recovered aromatic dicarboxylic acid.

SUMMARY OF THE INVENTION

The present inventors have made intensive investigations to solve the problems involved in the known methods of purifying a crude aromatic dicarboxylic acid, inclusive of terephthalic acid, and then recovering the thus purified acid, and established a new method wherein an aqueous solution of a water soluble organic amine salt of a crude aromatic dicarboxylic acid is first prepared and purified, and then the organic amine salt is thermally decomposed to regenerate the aromatic dicarboxylic acid. According to this method, the organic amine salt can be thermally decomposed at a lower temperature than the known ammonium salt, with substantially no by-production of an acid amide. The method therefore permits the recovery of highly purified aromatic dicarboxylic acid in a high yield with a small amount of energy. The invention has been accomplished based on these findings.

It is therefore an object of the invention to provide an industrially advantageous method of purifying a crude aromatic dicarboxylic acid and recovering the acid in a highly purified form in a high yield via an organic amine salt of the acid with a reduced amount of energy and with substantially no by-production of an acid amide.

DETAILED DESCRIPTION OF THE INVENTION

The invention provides a method of purifying a crude aromatic dicarboxylic acid, which comprises purifying an aqueous solution of an organic amino salt of the crude aromatic dicarboxylic acid, and then thermally decomposing the organic amine salt to recover the thus highly purified aromatic dicarboxylic acid.

The method is advantageously used, in particular, for recovery of an aromatic dicarboxylic acid from polyester resin which contains the acid and an alkylene glycol as structural units. Namely, the polyester is hydrolyzed in the presence of an organic amine to form an organic amine salt of the aromatic dicarboxylic acid, and the method is applied to the salt, thereby to recover the aromatic dicarboxylic acid having a high purity.

The aromatic dicarboxylic acid, to which the method of the invention is applicable includes a mononuclear aromatic dicarboxylic acid, such as terephthalic acid or isophthalic acid; a polynuclear aromatic dicarboxylic acid, such as naphthalenedicarboxylic acids or diphenyldicarboxylic acids. These aromatic dicarboxylic acids may have one or more alkyl groups as substituents on the aromatic nuclei. The alkyl group has preferably 1 to 3 carbons. However, terephthalic acid is typical of the aromatic dicarboxylic acids to which the method of the invention is preferably applicable.

The requisite for the organic amine used in the method of the invention is that it readily reacts with an aromatic dicarboxylic acid thereby to form a water soluble salt thereof, and further the thus formed water soluble organic amine salt is thermally decomposed at a relatively low temperature, to readily regenerate the aromatic dicarboxylic acid and the organic amine. It is preferred that the regenerated organic amine can be used repeatedly in the step for forming its salt of aromatic dicarboxylic acid.

The organic amine may be aliphatic, alicyclic, aromatic or heterocyclic amines. More specifically, the aliphatic amine includes a tertiary amine, preferably a trialkylamine wherein each of the three alkyls has independently 1 to 4 carbons, such as trimethylamine, triethylamine, tri-n-propylamine, triisopropylamine, dimethylethylamine, diethylmethylamine or diethylisopropylamine; a secondary amine, preferably a dialkylamine wherein each of the two alkyls has independently 1 to 4 carbons, such as dimethylamine, methylethylamine or diethylamine; and a primary amine, preferably an alkylamine wherein the alkyl has 1 to 4 carbons, such as methylamine, ethylamine, n-propylamine, isopropylamine, n-butylamine, isobutylamine or sec-butylamine.

The alicyclic amine includes a tertiary amine, preferably an N,N-dialkylaniline wherein each of the two alkyls has independently 1 to 4 carbons, such as N,N-dimethylcyclohexylamine, N,N-diethylcyclohexylamine or N,N-diisopropylamine; and a secondary amine, preferably an N-alkylcyclohexylamine wherein the alkyl has 1 to 4 carbons, such as N-methylcyclohexylamine, N-ethylcyclohexylamine or N-isopropylcyclohexylamine. A primary amine may also be used such as cyclohexylamine or cyclopentylamine which may be substituted by one or more lower alkyl groups of 1 to 4 carbons such as methyl or ethyl.

The aromatic amine includes a tertiary amine, preferably an N,N-dialkylaniline wherein each of the two alkyls has independently 1 to 4 carbons, such as N,N-dimethylaniline, N,N-diethylaniline or N,N-di butylaniline; or an N,N-dialkyltoluidine wherein each o f the two alkyls has independently 1 to 4 carbons, such a s N,N-dimethyltoluidine or N,N-diethyltoluidine.

The heterocyclic amine may be exemplified by, for example, pyridine, piperidine, pyrrolidine and their derivatives such as 2,6-1utidine, α-picoline, N-methylpiperidine or N-methylpyrrolidine.

Among the above mentioned, an aliphatic amine or an alicyclic amine or a mixture of these is particularly preferred.

In view of the requisite for the organic amine herein before mentioned, it is preferred that the organic amine used has a strong basicity and forms a salt of an aromatic dicarboxylic acid which is sufficiently water soluble, and in addition, the organic amine has resistance to thermally induced change in color and deterioration. When basicity is in particular regarded as important among the requisites, the use of an organic amine is preferred which has many electron-donating groups bonded to the nitrogen atom which forms an amino group. Hence, a secondary amine is preferred rather than a primary amine, and a tertiary amine rather than a secondary amine. Also from the stand-point that a salt of an aromatic dicarboxylic acid has generally a large solubility in water, as well as the salt is not accompanied by by-production of undesirable acid amide when it is thermally decomposed, a tertiary amine is preferred in the invention.

Accordingly, a tertiary amine is preferred such as trimethylamine or triethylamine among aliphatic amines, or such as N,N-dimethylcyclohexylamine is preferred among alicyclic amines.

An aqueous solution of an organic amine salt of crude aromatic dicarboxylic acid may be prepared, for instance, by admixing the acid with a slight excess of organic amine in a solution, followed by heating the mixture under stirring, if necessary, under an increased pressure, thereby to form the salt in the solution.

The method of forming an organic amine salt of a crude aromatic dicarboxylic acid as above set forth is already well known, and the method is not limited to any specific one. However, an organic amine is used usually in an amount of not less than 2 mole parts, preferably not less than 2.1 mole parts, per mole part of aromatic dicarboxylic acid. The use of not more than 3 mole parts per mole part of the acid is usually enough.

The reaction temperature at which an organic amine salt of aromatic dicarboxylic acid is formed is not specifically limited, but a suitable temperature may be readily selected so that the salt is formed. Usually an aromatic dicarboxylic acid is mixed with a slight excess of an organic amine in solution, and then the mixture is stirred at a suitable temperature which may be in the range of 0°–250° C. Preferably the reaction is carried out at a temperature of 30°–110° C., if necessary, under an increased pressure.

However, as set forth hereinafter, an aqueous solution of an organic amine salt of an aromatic dicarboxylic acid which is obtained by hydrolysis of polyester resin in the presence of an organic amine is advantageously used as a starting material according to the invention. The invention is very useful for use in recovery of highly purified aromatic dicarboxylic acid from such an aqueous solution of an organic amine salt of a crude aromatic dicarboxylic acid as above mentioned.

According to the invention, an aqueous solution of an organic amine salt of a crude aromatic dicarboxylic acid is first purified by a conventional method. For example, the solution is treated with an adsorbent such as activated carbon, or the organic amine salt is recrystallized. When the former method is employed, an organic amine salt of aromatic dicarboxylic acid may be first formed in a solution, and then activated carbon may be added to the solution, or an organic amine salt of aromatic dicarboxylic acid may be formed in a solution of the amine in the presence of activated carbon.

The amine salt of aromatic dicarboxylic acid is thus purified, and the solution thereof is then heated to thermally decompose the salt to liberate the aromatic dicarboxylic acid therefrom and precipitate the acid in the solution, followed by recovering the acid by a conventional means such as filtration. The decomposing temperature is usually in the range of 50°–180° C., preferably in the range of 90°–150° C.

An alkylene glycol, e.g., ethylene glycol, is one of the components which is formed together with an aromatic dicarboxylic acid when a polyester resin is hydrolyzed.

However, it is useful to add such an alkylene glycol to an aqueous solution of an organic amine salt of the acid prepared since the alkylene glycol raises the reflux temperature of the solution so that the salt is decomposed efficiently, thereby to improve the recovery rate of highly purified aromatic dicarboxylic acid.

An organic amine is readily oxidized when its salt is thermally decomposed so that it is not desirable that the atmosphere under which the thermal decomposition is effected contains an oxidative gas such as oxygen. From this point of view, it is preferred that the thermal decomposition of organic amine salt of aromatic dicarboxylic acid is effected under an inactive atmosphere such as of a nitrogen, argon or helium gas, or under a reductive atmosphere such as of a hydrogen or a lower hydrocarbon gas. An atmosphere composed of a mixture of an inactive gas and a reductive gas may be employed. It is also one of the preferred embodiments of the invention that the decomposition is effected under an atmosphere of steam which contains superheated steam. The steam may have a temperature of 100°–200° C. and a pressure of 1–15.3 atmospheric pressure.

For example, as one of the embodiments according to the invention, an aqueous solution of an organic amine salt of aromatic dicarboxylic acid is purified, the solution is distilled to remove water (and if any, an alkylene glycol) therefrom and concentrated, and then while steam which contains superheated steam is blown into the resultant residue or concentrate to heat and decompose the organic amine salt, the regenerated organic amine is distilled together with water, whereupon the regenerated aromatic dicarboxylic acid precipitates. Then, the precipitate is collected, washed with water and dried, and thus the aromatic dicarboxylic acid having a high purity is recovered.

As set forth hereinbefore, such an organic amine is preferred as has resistance to thermally induced change in color and deterioration so that the amine regenerated by thermal decomposition of amine salt of aromatic dicarboxylic acid is repeatedly used to form an organic amine salt of an aromatic dicarboxylic acid.

The method of the invention is especially useful for recovery of aromatic dicarboxylic acid, in particular, terephthalic acid, by hydrolysis of polyester resin composed of structural units of aromatic dicarboxylic acid and alkylene glycol, typically such as polyethylene terephthalate resin or polybutylene terephthalate resin. If necessary, the alkylene glycol is also recovered in a highly purified form.

The polyester resin to which the method of the invention is applicable contains an aromatic dicarboxylic acid and an alkylene glycol as structural units. As hereinbefore set forth, the aromatic dicarboxylic acid includes, for example, a mononuclear aromatic dicarboxylic acid such as terephthalic acid or isophthalic acid, and a polynuclear aromatic dicarboxylic acid such as naphthalene-dicarboxylic acids or diphenyldicarboxylic acids. These aromatic dicarboxylic acids may have one or more alkyl groups as substituents on the armatic nuclei. The alkyl group has preferably 1 to 3 carbons. Terephthalic acid is typical of the aromatic dicarboxylic acids.

The alkylene glycol may be exemplified by, for example, ethylene glycol or butylene glycol.

Accordingly, the method of the invention is in particular suitably applicable to polyethylene terephthalate resin, polybutylene terephthalate resin or polyethylene naphthalenedicarboxylate resin among the polyester resins.

According to the invention, therefore, such a polyester resin is hydrolyzed under heating in an aqueous solution of an organic amine making use of the organic amine as a hydrolysis assistant, thereby to form a water soluble organic amine salt of aromatic dicarboxylic acid, the aqueous solution containing such a water soluble amine salt therein is purified as before described, and then the salt is thermally decomposed, whereupon the aromatic dicarboxylic acid can be recovered as precipitates in a high purity.

The resultant mother liquor contains an alkylene glycol, and if necessary, the alkylene glycol is also recovered in a highly purified form by conventional means such as distillation.

The hydrolysis of polyester resin is usually effected in water by heating the resin at a temperature in the range of 100°–250° C., preferably in the range of 150°–210° C., under an increased pressure in the presence of an organic amine. The resultant aromatic dicarboxylic acid forms an amine salt as the acid is generated by the hydrolysis.

In this way, the polyester resin is hydrolyzed to form an organic amine salt, the salt is thermally decomposed to regenerate an aromatic dicarboxylic acid, and the acid is recovered. The mother liquor contains an alkylene glycol. Thus, if necessary, the mother liquor is heated at a temperature of 95°–110° C. usually under normal pressures to distill the water off, and then the resultant concentrate is distilled under reduced pressures to recover the alkylene glycol having a high purity. When the alkylene glycol is ethylene glycol, the distillation of the concentrate is carried out usually at a temperature of 70°–180° C. and under a pressure of 5–100 mmHg. When an alkylene glycol has a high boiling temperature, the concentrate is preferably distilled under a more reduced pressure to prevent deterioration of the glycol.

The method of the invention for purifying a crude aromatic dicarboxylic acid makes use of an organic amine salt of the acid, and the salt thermally decomposes at a lower temperature than the ammonium salt used in the known method, with substantially no undesirable by-production of an acid amide, and hence the method permits efficient recovery of highly purified aromatic dicarboxylic acid in a high yield in an industrially advantageous manner. More specifically, according to the invention, an aqueous solution of an organic amine salt of terephthalic acid, for example, is refluxed under heating to decompose the amine salt, and the regenerated terephthalic acid is recovered. Thus, the method needs only about a half of energy per unit of terephthalic acid compared with the known method wherein the ammonium salt is used. The time needed is also about two thirds of the time needed in the known method.

As a further advantage of the invention, the organic amine is not substantially consumed and can be used repeatedly for forming a salt with an aromatic dicarboxylic acid. The method of the invention can be readily practiced in a so-called closed system with substantially no escape of organic amine into the air or waste water, in contrast to the known method which uses ammonia in place of organic amine.

As a still further advantage of the invention, polyester resin is hydrolyzed at a lower temperature and under a lower pressure than in the known method in which ammonia is used, and then the resultant solution is purified, so that a highly purified aromatic dicarboxylic acid can be recovered more efficiently and in a higher yield. In addition, when the polyester resin contains ethylene glycol as alkylene glycol units, the method makes it possible to recover highly purified ethylene glycol in a high yield with the by-production of diethylene glycol being suppressed, and hence the method is advantageous from the industrial standpoint.

The invention will now be described with reference to examples, however, the invention is not limited thereto.

EXAMPLE 1

An amount of 96.0 g of crushed green bottles composed of polyethylene terephthalate for a soft drink was hydrolyzed to provide terephthalic acid, an aqueous solution of trimethylamine salt of terephthalic acid was prepared by use of 83.0 g (0.5 mole) of the terephthalic acid, 216.3 g of an aqueous solution of trimethylamine (having a concentration of 30% by weight and containing 1.1 mole of the amine) and 31.0 g (0.5 mole) of ethylene glycol. An amount of 5 g of activated carbon was added to the solution, and the solution was stirred for 15 minutes at room temperature under normal pressure.

The activated carbon was removed by filtration from the solution, and the resultant colorless filtrate was heated under reflux at a temperature of about 100° C. under a stream of nitrogen for 3 hours under normal pressure. Thereafter the resultant precipitates were collected by filtration, washed with water and dried to provide 79.3 g of colorless terephthalic acid having a purity of 99.9% in a recovery rate (yield) of 95.5%.

An amount of 7.5 g of the thus obtained terephthalic acid was dissolved in 50 ml of 2 Normal (2N) aqueous solution of potassium hydroxide and the transmittance at a wavelength of 340 nm and 400 nm (referred to hereinafter as the alkaline transmittance) was measured. The transmittance was found to be the same as commercially available pure terephthalic acid.

The trimethylamine liberated from the trimethylamine salt of terephthalic acid by the thermal decomposition thereof was found to be reusable for forming a salt of crude terephthalic acid from other sources.

EXAMPLE 2

An amount of 96.0 g of crushed green bottles composed of polyethylene terephthalate for a soft drink was hydrolyzed to provide terephthalic acid. A mixture of 83.0 g (0.5 mole) of the terephthalic acid, 117.7 g (1.1 mole) of 2,6-lutidine, 31.0 g (0.5 mole) of ethylene glycol and 749 g of water was heated to 40° C. to prepare an aqueous solution of 2,6-lutidine salt of terephthalic acid. An amount of 5 g of activated carbon was added to the solution, and the solution was stirred at 40° C. for 30 minutes under normal pressure.

The activated carbon was removed by filtration from the solution to provide a colorless filtrate. The filtrate was distilled at a temperature of 97°–110° C. under normal pressure and a stream of nitrogen to remove a mixture of water-lutidine (650 g). The resultant precipitates were collected by filtration, washed with water and dried to provide 78.6 g of colorless terephthalic acid having a purity of 99.9% in a recovery rate of 94.7%.

EXAMPLE 3

An amount of 96.0 g of crushed green bottles composed of polyethylene terephthalate for a soft drink was hydrolyzed to provide terephthalic acid. An aqueous solution of trimethylamine salt of terephthalic acid was prepared by use of 83.0 g (0.5 mole) of the terephthalic acid, 216.3 g of an aqueous solution of trimethylamine (having a concentration of 30% by weight and containing 1.1 mole of the amine). An amount of 5 g of activated carbon was added to the solution, and the solution was stirred for 15 minutes at room temperature under normal pressure.

The activated carbon was removed by filtration from the solution, and the resultant colorless filtrate was heated under reflux at a temperature of about 100° C. under a stream of nitrogen for 5 hours under normal pressure. Thereafter the resultant precipitates were collected by filtration, washed with water and dried to provide 52.2 g of colorless terephthalic acid having a purity of 99.9% in a recovery rate of 62.9%.

The thus recovered terephthalic acid was found to have the same alkaline transmittance as commercially available pure terephthalic acid.

Comparative Example 1

A mixture of 83.0 g (0.5 mole) of crude terephthalic acid, 200 g of ammonia water (having a concentration of 25% by weight), 31.0 g (0.5 mole) of ethylene glycol and 600 g of water was heated to 50° C. to prepare an aqueous solution of ammonium terephthalate. An amount of 5 g of activated carbon was added to the solution, and the solution was stirred at 50° C. for 30 minutes under normal pressure.

The activated carbon was removed by filtration from the solution to provide a colorless filtrate. After the filtrate was heated under reflux at a temperature of about 100° C. for 5 hours under a stream of nitrogen, 1000 g of water was added to the reaction mixture, followed by allowing it to stand to cool with stirring. The resultant precipitates were collected by filtration, washed with water and dried to provide 22.4 of colorless terephthalic acid in a recovery rate of 27.0%.

The resultant mother liquor and the wash were combined together and made acidic with sulfuric acid. The resultant precipitates were collected by filtration, washed with water and dried to provide 59.7 g of terephthalic acid. The recovery rate was found to be 71.9%.

The above result shows that after heating the aqueous solution of ammonium terephthalate under reflux for 5 hours, terephthalic acid was found to remain in the form of an ammonium salt and was found in the filtrate and wash.

EXAMPLE 4

Crushed green bottles composed of polyethylene terephthalate for a soft drink was hydrolyzed to provide terephthalic acid. An amount of 83.0 g (0.5 mole) of the terephthalic acid, 216.3 g of an aqueous solution of trimethylamine (having a concentration of 30% by weight and containing 1.1 mole of the amine) and 193.7 g (3.1 mole) of ethylene glycol were mixed together at normal temperature to prepare an aqueous solution of trimethylamine salt of terephthalic acid. An amount of 5 g of activated carbon was added to the solution, and the solution was stirred for 15 minutes at room temperature under normal pressure.

The activated carbon was removed by filtration from the solution, and the resultant colorless filtrate was distilled to remove water therefrom. Steam of 135° C. and 3 atmospheric pressures was blown into the resultant concentrate at a rate of 130 g/hr. over 2 hours to remove trimethylamine together with water.

The resultant precipitates were collected by filtration, washed with water and dried to provide 80.6 g of colorless terephthalic acid having a purity of 99.9% in a recovery rate of 97.0%.

The thus recovered terephthalic acid was found to have the same alkaline transmittance as commercially available pure terephthalic acid.

The trimethylamine recovered from the solution of the amine salt was found to be reusable for forming a salt of crude terephthalic acid from other sources after suitably adjusting the concentration.

What is claimed is:

1. A method of purifying a crude terephthalic acid which comprises the following steps:
   (A) forming an aqueous solution of an organic amine salt of the terephthalic acid;
   (B) removing impurities from the aqueous solution of organic amine salt of the terephthalic acid; and
   (C) thermally decomposing the organic amine salt in the presence of an alkylene glycol and recovering highly purified terephthalic acid.

2. The method as claimed in claim 1 wherein the organic amine is a trialkylamine wherein each of the three alkyls has independently 1 to 4 carbons.

3. The method as claimed in claim 2 wherein the trialkyl amine is trimethylamine.

4. The method as claimed in claim 1 wherein the organic amine is a dialkyl amine wherein each of the two alkyls has independently 1 to 4 carbons.

5. The method as claimed in claim 1, wherein said thermal decomposing occurs at a temperature of 50°–180° C.

6. The method as claimed in claim 1, wherein said thermal decomposing occurs under an atmosphere of an inactive gas, a reductive gas, or steam.

7. The method as claimed in claim 1, wherein said thermal decomposing comprises:
   (1) removing water from the aqueous solution of organic amine salt of terephthalic acid by distillation to form a concentrated solution;
   (2) blowing steam into the concentrated solution and thereby thermally decomposing the organic amine salt in the presence of an alkylene glycol; and
   (3) removing the resulting organic amine together with water from the concentrated solution and recovering the terephthalic acid as a residue.

8. The method as claimed in claim 7 wherein the organic amine is trimethylamine.

9. The method as claimed in claim 1, wherein said removing impurities comprises contacting said aqueous solution with activated carbon.

10. The method as claimed in claim 1, wherein said recovering comprises collecting the aromatic dicarboxylic acid, regenerating the organic amine, and circulating a part or all of the regenerated organic amine to the step for forming the organic amine salt of the aromatic dicarboxylic acid.

11. The method as claimed in claim 1, wherein said forming of said organic amine salt of said terephthalic acid comprises hydrolyzing polyester resin which contains terephthalic acid and an alkylene glycol as structural units in the presence of an organic amine to form a water soluble organic amine salt of the terephthalic acid.

12. The method as claimed in claim 11, wherein said thermal decomposing occurs at a temperature of 50°–180° C.

13. The method as claimed in claim 11 or 12 wherein the organic amine is a trialkylamine wherein each of the three alkyls has independently 1 to 4 carbons.

14. The method as claimed in claim 13 wherein the trialkylamine is trimethylamine.

* * * * *